United States Patent [19]

Hester, Jr.

[11] 4,075,221

[45] Feb. 21, 1978

[54] PROCESS FOR PREPARING TRIAZOLOBENZODIAZEPINES

[75] Inventor: Jackson B. Hester, Jr., Galesburg, Mich.

[73] Assignee: The Upjohn Company, Kalamazoo, Mich.

[21] Appl. No.: 761,803

[22] Filed: Jan. 24, 1977

[51] Int. Cl.² ............................................. C07D 487/04
[52] U.S. Cl. ........................... 260/308 R; 260/294.8 B; 260/296 T
[58] Field of Search ......... 260/308 R, 296 T, 294.8 B

[56] References Cited
U.S. PATENT DOCUMENTS 4,001,262  1/1977  Gall .................................. 260/308 R Primary Examiner—Alton D. Rollins
Attorney, Agent, or Firm—Hans L. Berneis

[57] ABSTRACT

An improved process for the production of 1-dialkyl-amino-ethyl-6-aryl-4H-s-triazolo[4,3-a][1,4]benzodiazepines of the formula II:

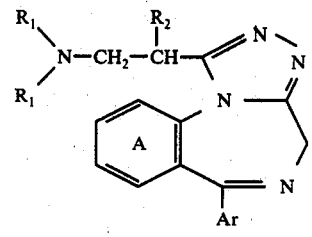

wherein $R_1$ is alkyl of 1 to 3 carbon atoms, inclusive; wherein $R_2$ is hydrogen, methyl or phenyl; wherein the ring A is unsubstituted, or monosubstituted with fluoro, chloro, bromo, nitro, trifluoromethyl or methylthio; and wherein Ar is phenyl; o-chlorophenyl; o-fluorophenyl; 2,6-difluorophenyl or 2-pyridyl, is carried out by reacting a compound of the Formula I:

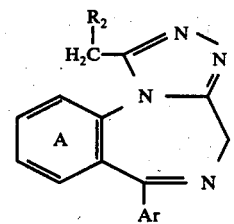

wherein ring A, Ar and $R_2$ are defined as above, with a dialkylmethyleneammonium salt in the presence of a reactive carboxylic acylating agent.

The compounds of Formula II ($R_2$=H) are known compounds (Belgian Pat. No. 782,84g) which have sedative-tranquilizing as well as pronounced antidepressant activity, suitable for the treatment of anxieties and depressions in mammals, including man.

14 Claims, No Drawings

PROCESS FOR PREPARING TRIAZOLOBENZODIAZEPINES

BACKGROUND OF THE INVENTION

1. Field of the Invention

This invention is concerned with an improved process for the production of 1-[2-(dialkylamino)ethyl]-6-aryl-4H-s-triazolo[4,3-a][1,4]benzodiazepines (II), and more specifically for the production of 8-chloro-1-[2-(dimethylamino)ethyl]-6-phenyl-4H-s-triazolo[4,3-a][1,4]benzodiazepine (IIC).

The compound, 8-chloro-1-[2-(dimethylamino)ethyl]-6-phenyl-4H-s-triazolo[4,3-a][1,4]benzodiazepine (IIC) has been produced earlier in low yields by a variety of processes, e.g., in Ser. No. 550,120, filed Feb. 14, 1975, now U.S. Pat. No. 4,012,413, it is prepared by reduction of the corresponding acetamide:

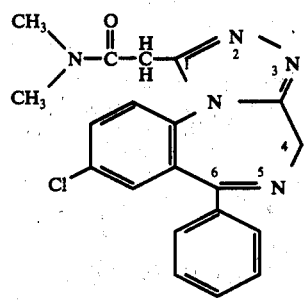

with borane, which produces simultaneous reduction of the 5,6-double bond and thus requires an additional oxidation step for the re-introduction of said double bond.

Another synthesis shown in this application Ser. No. 550,120 is the condensation of the 2-hydrazino compound:

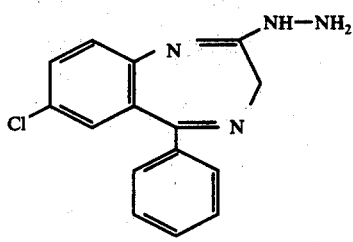

with β-phthalimidopropionic acid:

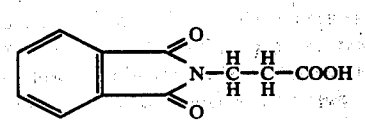

which provides:

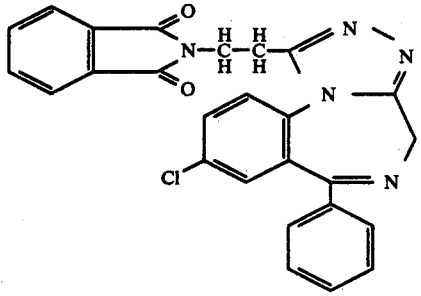

which upon treatment with hydrazine followed by reductive alkylation with formaldehyde provides the desired compound IIC. In the first of these two methods, compound IIC was obtained in yields of less than 15%. In the second method, although the overall yield was higher (35%-45%), several steps were involved and the large scale preparation of IIC was made difficult by the apparent instablity of the primary amine intermediate.

In application Ser. No. 657,461, now abandoned, a compound of the formula:

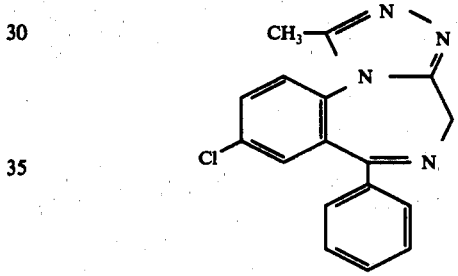

is reacted under neutral conditions with a dimethylmethyleneammonium salt to give compound IIC in a yield of 20% to 30%. This process required heating the reactants at temperatures of from 50°-90° C. for from 1-2 days. It was usually necessary to separate the product (IIC) from biproducts and unreacted starting material by chromatography, an additional costly step unsuitable for large scale preparations.

It has now been discovered that compound IIC can be produced in yields of greater than 80%, when with the dimethylmethyleneammonium salt an acylating agent, such as a carboxylic acid halide or the anhydride of a strongly acidic carboxylic acid is used in catalytic amounts (5%-50%) of the molequivalents of the 1-methyl-6-phenyl-4H-s-triazolo[4,3-a][1,4]benzodiazepine; alternatively, the dimethylmethyleneammonium salt can be prepared in situ, by reacting N,N,N',N',-tetramethyldiaminomethane with an acyl halide or acid anhydride, with the latter being in slight excess to fulfill the conditions for the presence of acyl halide or acid anhydride.

The new reaction can therefore be illustratively presented as follows:

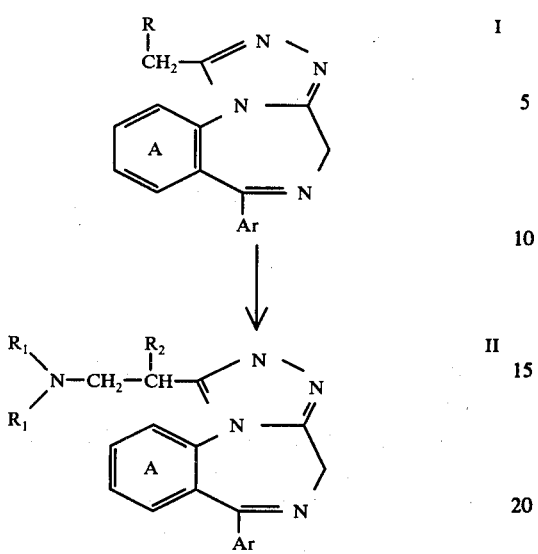

wherein $R_1$ is alkyl of 1 to 3 carbon atoms, inclusive; wherein $R_2$ is hydrogen, methyl or phenyl; wherein the ring A is unsubstituted, or monosubstituted with fluoro, chloro, bromo, nitro, trifluoromethyl or methylthio and wherein Ar is phenyl, o-chlorophenyl, o-fluorophenyl, 2,6-difluorophenyl, or 2-pyridyl.

The process of this invention comprises:

Treating a compound of formula I with an equivalent or slightly (5%–10%) larger amount of a selected dialkylmethyleneammonium salt which can be:

(A) prepared in advance by reacting N,N,N',N',-tetraalkyldiaminomethane and an acylating agent, such as,

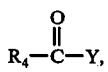

wherein $R_4$ is phenyl or alkyl of 1 to 5 carbon atoms, inclusive, in which the alkyl moiety can be chlorinated or fluorinated and Y is chloro or bromo, or with an acid anhydride of the formula

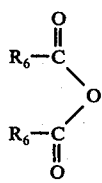

wherein $R_6$ is defined as a chloro or fluoro-substituted alkyl of 1 to 5 carbon atoms, or even an alkyl chloroformate of the formula:

ClCOOR' wherein R' is a lower alkyl of 1 to 4 carbon atoms.

(B) prepared in situ by the same reaction as shown under (A).

In either case the presence of a slight excess of the acylating agent, being between 5% and 50% molar excess over the calculated stoichiometric amount of N,N,N',N'-tetraalkyldiaminomethane, causes the reaction to proceed faster at a lower temperature and to a higher yield.

DESCRIPTION OF THE PREFERRED EMBODIMENT OF THE INVENTION

The invention is directed to an improved process for the production of compounds of the formula II:

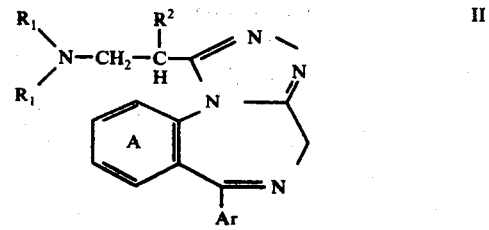

wherein $R_1$ is alkyl of 1 to 3 carbon atoms, inclusive; wherein $R_2$ is hydrogen, methyl or phenyl; wherein the ring A is unsubstituted or monosubstituted with fluoro, chloro, bromo, nitro, trifluoromethyl or methylthio; and wherein Ar is phenyl, o-chlorophenyl, o-fluorophenyl, 2,6-difluorophenyl or 2-pyridyl.

The more preferred process in this invention is essentially directed to the production of the more preferred compounds which are of the formula IIA;

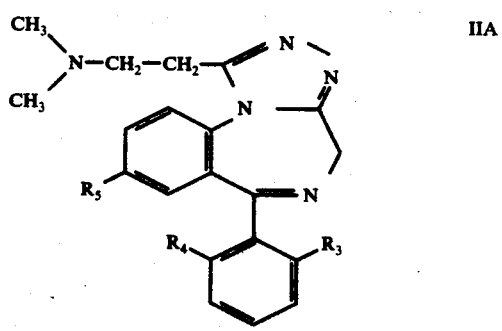

wherein $R_3$ is hydrogen, chloro or fluoro; and wherein $R_4$ is hydrogen, or fluoro, providing $R_3$ is not chloro; wherein $R_5$ is hydrogen, fluoro, chloro, trifluoromethyl or methylthio.

The most preferred compounds resulting from this process are of the structure IIB:

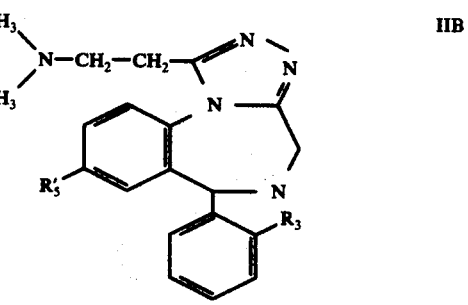

wherein $R_3$ is hydrogen, chloro or fluoro, and wherein $R_5'$ is fluoro, chloro or trifluoromethyl.

The compounds of formula II (including the preferred compounds of formula IIA and IIB), as well as their pharmacologically acceptable acid addition salts, have anti-anxiety, sedative and tranquilizing properties, but are even more interesting for their pronounced anti-depressant activity, which makes these compounds useful in the treatment of depressed humans or other mammals.

The activity, utility and method of use of these compounds is described in detail in U.S. application Ser. No. 550,120, filed Feb. 14, 1975, and particularly in U.S. Pat. No. 3,969,504.

The starting compounds of formula I for this invention are prepared as shown in U.S. Pat. Nos. 3,987,052 and 3,734,922.

In carrying out the process of this invention, a starting compound of formula I in a suitable organic solvent is treated with a dialkylmethyleneammonium salt either freshly prepared or prepared in situ by the reaction of N,N,N',N'-tetraalkyldiaminomethane and an acylating agent. As solvent, methylene chloride, chloroform, tetrahydrofuran, dimethylformamide, dioxane, dimethoxyethane, hexamethylphosphoramide, tetramethylurea, dimethylacetamide, and the like can be used. The acylating agent is usually a compound of the formula

wherein Y is chloro or bromo and $R_4$ is phenyl or alkyl of 1 to 5 carbon atoms, inclusive, in which the alkyl group can be chlorinated or fluorinated. Acetyl-chloride and bromide are preferred in this group. Also useful are the halides of carbonic acid monoesters, e.g., ethyl chloroformate or anhydrides of strongly acidic carboxylic acids, e.g., trifluoroacetic anhydride. The acylating agents defined above react with N,N,N',N'-tetraalkyldiaminomethane to give the effective reagent, a dialkylmethyleneammonium salt

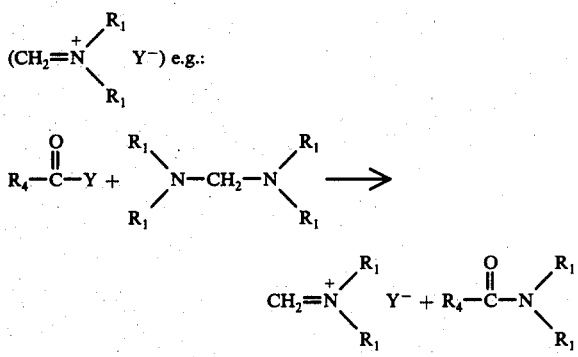

$R_1$ = alkyl as defined above

The reaction to provide the dialkylmethylene ammonium salt requires merely equimolar amounts of the acylating agent and N,N,N',N'-tetraalkyldiaminomethane. The improvement in yield of the final product II which is the present invention, is achieved when the reagent

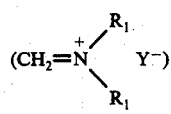

is reacted with about an equimolar or lesser quantity of the starting compound, the triazolobenzodiazepine (I), but with a 5% to 50% molar excess of the acylating component

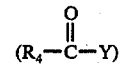

present in the final reaction mixture. This can be done either by adding the excess acylating agent

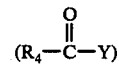

to a mixture of the preformed reagent

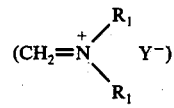

and a solution of the starting compound, or by preparing the reagent in situ by adding a 5% to 50% molar excess of the acylating agent

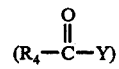

to the mixture of the starting compound and the N,N,N',N'-tetraalkyldiaminomethane.

The reaction temperature is also important for this reaction and the temperature required depends upon the acylating agent employed, namely:

The reaction is generally performed between −30° and 50° C. and requires then between ½ to 24 hours. In the preferred embodiment of the invention, when acetyl chloride is used as the acylating agent, temperatures of between −10° and +10° C. and reaction periods of 0.5 to 2 hours are employed. However, if benzoyl chloride instead of acetyl chloride is employed, temperatures of 25° C. and 6 to 24 hours reaction times are preferred. The product II obtained is purified by conventional methods, e.g., extraction, chromatography and recrystallization.

The dimethylmethyleneammonium salts can be prepared in one of the manners described in the literature, e.g., H. Bohme et al., Chem. Ber. 93, 1305 (1960);
J. Schreiber et al., Angew. Chem. int. ed. 10, 330 (1971);
H. Bohme, Tetrahedron Lett. 2785 (1972);
H. Volz et al., Tetrahedron Lett. 1917 (1970); ibid., Ann. Chem. 752, 86 (1971);
R. Huisgen et al., Tetrahedron Lett. 783 (1965);
A. Ahond et al., J. Amer. Chem. Soc. 90, 5622 (1968);
Y. Jaser, Chem. Comm. 253 (1974).

The same reagent is used when prepared in situ, i.e., the acylating agent and N,N,N',N'-tetraalkyldiaminomethane are reacted together with the selected triazolobenzodiazepine I starting compound present, and for this particular improved reaction, with an excess of the specific acylating agent present as discussed above.

The following examples illustrate the novel process, but are not to be construed as limiting.

EXAMPLE 1

8-Chloro-1-[2-(dimethylamino)ethyl]-6-phenyl-4H-s-triazolo[4,3-a][1,4]benzodiazepine p-toluenesulfonate.

A stirred solution of 8-chloro-1-methyl-6-phenyl-4H-s-triazolo[4,3-a][1,4]benzodiazepine (3.09 g., 0.01 mole) in dry dimethylformamide (50 ml.) was cooled in an ice bath, under nitrogen, and treated successively with N,N,N',N'-tetramethyldiaminomethane (1.229 g., 0.012 mole) and dropwise with acetyl chloride (0.923 ml., 0.013 mole). The cloudy mixture was kept in the ice bath for 1 hour and 55 minutes and poured into a mixture of ice and saturated sodium bicarbonate. The solution was saturated with sodium chloride and extracted five times with chloroform. The extracts were washed with brine, dried over anhydrous sodium sulfate and concentrated in vacuo using xylene and toluene to help remove residual dimethylformamide. A solution of the resulting oil in absolute ethanol was acidified to a pH 3.5–4 with a solution of p-toluenesulfonic acid (1 equivalent) in absolute ethanol. The remaining salt was crystallized to give 8-chloro-1-[2-(dimethylamino)ethyl]-6-phenyl-4H-s-triazolo[4,3-a][1,4]benzodiazepine p-toluenesulfonate in three crops: 3.69 g. of melting point 196°–197° C., 0.612 g. of melting point 197°–198° C. and 0.022 g. of melting point 198.5°–199° C. The total yield was 79.9%. Ethanol crystallization of this material usually results in a product which contains residual ethanol or water. To remove the solvent, the first two crops (4.3 g.) were combined, recrystallized once from 95%–100% ethanol, redissolved in 95% ethanol and added slowly to boiling toluene at such a rate that the temperature of the distilling azeotrope remained between 85°–95° C. The level of the boiling mixture was maintained constant by the addition of fresh toluene. After the addition the temperature of the distillate was allowed to rise to 108° C. The mixture was cooled and the finely divided 8-chloro-1-[2-(dimethylamino)ethyl]-6-phenyl-4H-s-triazolo[4,3-a][1,4]benzodiazepine was collected by filtration to give 3.747 g. of melting point 199°–199.5° C.

Anal. Calcd. for $C_{27}H_{28}ClN_5O_3S$: C, 60.27; H, 5.24; Cl, 6.59; N, 13.02; S, 5.96 Found: C, 60.52; H, 5.34; Cl, 6.57; N, 13.43; S, 6.13

The examples given in the chart on the following page were performed in a manner similar to that shown in Example 1 but varying the acylating agent 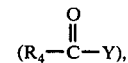 ($R_4$—C(O)—Y), solvent, reaction time and temperature.

TABLE

| Example Number | $R_4$—C(O)—Y | Amount[1] | $CH_2(N(CH_3)_2)_2$ [2] | t[4] | T(C°)[5] | Solvent | Yield %[3] |
|---|---|---|---|---|---|---|---|
| 2 | $CH_3$—CCl(O) | 2.34 | 2.2 | 65 min. | 0° | DMF[7] | 82.8 |
| 3 | $CH_3$—CCl(O) | 1.3 | 1.2 | 190 min. | 0° | THF[8] | 89.4 |
| 4 | $CH_3$CCl(O) | 1.3 | 1.2 | 190 min. | 0° | $CH_2Cl_2$ | 85.9 |
| 5 | EtOCCl(O) | 1.3 | 1.2 | 300 min. | 0° | $CH_2Cl_2$ | 53.7 |
| 6 | $(CF_3C)_2O$ | 1.4 | 1.2 | 95 min. | 0° | THF[8] | 68.9 |
| 7 | $\phi$—CCl(O) [6] | 1.4 | 1.2 | 1.5 hr. 21.5 hr. | 0° 25° | THF[8] | 85.6 |

(1) Molar equivalents of $R_4$—C(O)—Y relative to 8-chloro-1-methyl-6-phenyl-4H-s-triazolo[4,3-a][1,4]benzodiazepine (2) Molar equivalents of N,N,N'N'-tetramethyldiaminomethane relative to 8-chloro-1-methyl-6-phenyl-4H-s-triazolo[4,3-a][1,4]benzodiazepine (3) Yield of 8-chloro-1-[2-(dimethylamino)ethyl]-6-phenyl-4H-s-triazolo[4,3-a][1,4]benzodiazepine p-toluenesulfonate isolated by direct crystallization from ethanol.

(4) Reaction time
(5) Reaction temperature
(6) $\phi$ = phenyl
(7) dimethylformamide
(8) tetrahydrofuran

EXAMPLE 8

8-Chloro-1-[2-(dimethylamino)ethyl]-6-phenyl-4H-s-triazolo[4,3-a][1,4]benzodiazepine p-toluenesulfonate A stirred solution of N,N,N',N'-tetramethyldiaminomethane (2.244 g., 0.022 mole) in dry dimethylformamide (50 ml.) was cooled in an ice bath and treated dropwise with acetyl chloride (1.65 ml., 0.023 mole). The ice bath was removed and the mixture was kept at 25° for 45 min. and treated with 8-chloro-1-methyl-6-phenyl-4H-s-triazolo[4,3-a][1,4]benzodiazepine (3.09 g., 0.01 mole). After 30 min. the mixture was poured into ice water, made alkaline with sodium bicarbonate, saturated with sodium chloride and extracted with chloroform. The extract was washed with a dilute salt solution, dried over anhydrous sodium sulfate and concentrated in vacuo using xylene and toluene to help remove residual dimethylformamide. A solution of the residue in ethanol was acidified with a solution of one equivalent of p-toluenesulfonic acid in ethanol and crystallized to give 8-chloro-1-[2-(dimethylamino)ethyl]-6- phenyl-4H-s-triazolo[4,3-a][1,4]benzodiazepine p-toluenesulfonate in three crops; 2.69 g. of melting point 195°–196° C.; 0.751 g. of melting point 192°–195.5° C. and 0.033 g. of melting point 195°–197° C. The total yield was 64.6%.

EXAMPLE 9

8-Chloro-1-[2-(dimethylamino)ethyl]-6-phenyl-4H-s-triazolo[4,3-a][1,4]benzodiazepine p-toluenesulfonate A stirred solution of N,N,N',N'-tetramethyldiaminomethane (1.637 ml., 0.012 mole) in dry diethyl ether (50 ml.) was cooled in an ice bath and treated, dropwise with acetyl chloride (0.852 ml., 0.012 mole). The ice bath was removed and the suspension was allowed to stand for 1 hr. The ether was removed by means of a filter stick and the white solid was washed several times with ether.

The resulting solid, dimethylmethyleneammonium chloride, was suspended in tetrahydrofuran, cooled in an ice bath, treated with 8-chloro-1-methyl-6-phenyl-4H-s-triazolo[4,3-a][1,4]benzodiazepine (3.09 g., 0.01 mole; and then dropwise with acetyl chloride (0.07 ml., 0.001 mole). This mixture was kept in the ice bath for 3 hours, poured into ice cold, dilute sodium bicarbonate and extracted with methylene chloride. The extract was washed with a dilute salt solution, dried over anhydrous sodium sulfate and concentrated in vacuo. A solution of the residual oil in ethanol was treated with a solution of 1 equivalent of p-toluenesulfonic acid in ethanol and the 8-chloro-1-[2-(dimethylamino)ethyl]-6-phenyl-4H-s-triazolo[4,3-a][1,4]benzodiazepine p-toluenesulfonate was isolated by crystallization.

EXAMPLE 10

8-Chloro-1-[2-(dimethylamino)-1-phenylethyl]-6-phenyl-4H-s-triazolo[4,3-a][1,4]benzodiazepine A stirred solution of 8-chloro-1-benzyl-6-phenyl-4H-s-triazolo[4,3-a][1,4]benzodiazepine (3.85 g., 0.01 mole) in dry dimethylformamide (50 ml.) was cooled, under nitrogen, in an ice bath and treated with N,N,N',N',-tetramethyldiaminomethane (1.229 g., 0.012 mole) and then dropwise with acetyl chloride (0.923 ml., 0.013 mole). The mixture was kept in the ice bath for 2 hours, poured into a mixture of ice and saturated aqueous sodium bicarbonate solution and extracted several times with chloroform. The extracts were washed with a dilute aqueous sodium chloride solution, dried over anhydrous sodium sulfate and concentrated in vacuo using xylene and toluene to help remove dimethylformamide. The residue was chromatographed on silica gel (200 g.) with methanol. The product thus obtained was crystallized from diethylether to give 8-chloro-1-[2-(dimethylamino)-1-phenylethyl]-6-phenyl-4H-s-triazolo[4,3-a][1,4]benzodiazepine in six crops; 0.483 g. of melting point 168.5°–170° C; 1.436 g. of melting point 169°–170.5° C. and 0.471 g. of melting point 169°–170.5° C., 0.530 g. of melting point 168.5°–170° C.; 0.231 g. of melting point 169°–170° C. and 0.269 g. of melting point 169°–170.5° C. The analytical sample was crystallized from ethyl acetate-Skellysolve B hexanes and had a melting point of 169.5°–171.5° C.

Anal. Calcd. for $C_{26}H_{24}ClN_5$: C, 70.66; H, 5.47; Cl, 8.02; N, 15.85 Found: C, 70.93; H, 5.55; Cl, 8.07; N, 15.86

EXAMPLE 11

8-Chloro-1-[[2-(dimethylamino)-1-methyl]ethyl]-6-phenyl-4H-s-triazolo[4,3-a][1,4]benzodiazepine; 8-chloro-4-[(dimethylamino)methyl]-1-ethyl-6-phenyl-4H-s-triazolo[4,3-a][1,4]benzodiazepine p-toluenesulfonate A stirred solution of 8-chloro-1-ethyl-6-phenyl-4H-s-triazolo[4,3-a][1,4]benzodiazepine (3.23 g., 0.01 mole) in warm dimethylformamide (50 ml.) was cooled in an ice bath under nitrogen; some of the starting compound precipitated. The mixture was treated with N,N,N',N'-tetramethyldiaminomethane (1.229 g., 0.012 mole) and then dropwise with acetyl chloride (0.923 ml., 0.013 mole). It was kept in the ice bath for 1 hour and 20 minutes and at ambient temperature (25° C.) for 3 hours. By thin layer chromatography the reaction did not go at 0° C. but went smoothly at ambient temperature; all solids had dissolved after 2.5 hours at about 25° C. The mixture was poured into ice water, neutralized with saturated aqueous sodium bicarbonate solution and extracted with chloroform. The extracts were washed with brine, dried over anhydrous sodium sulfate and concentrated in vacuo using xylene to help remove dimethylformamide. The residue was chromatographed on silica gel (200 g.) with methanol. The slower moving material was dissolved in ethyl acetate and acidified with a solution of p-toluenesulfonic acid in ethanol. The salt was crystallized from ethanol-ethyl acetate to give 8-chloro-4-[(dimethylamino)methyl]-1-ethyl-6-phenyl-4H-s-triazolo[4,3-a][1,4]benzodiazepine p-toluenesulfonate, in two crops: 0.864 g. of melting point 210°–210.5° C. (dec.) and 0.829 g. of melting point 209.5°–210° C. (dec.). The analytical sample had a melting point of 209°–210° C. dec.

Anal. Calcd. for $C_{28}H_{30}ClN_5O_3S$: C, 60.92; H, 5.48; Cl, 6.42; N, 12.68; S, 5.81 Found: C, 60.92; H, 5.45; Cl, 6.87; N, 12.70; S, 5.74

The mother liquors from the tosylate crystallization were concentrated and neutralized with aqueous sodium bicarbonate solution. The free base, thus obtained, was combined with the faster moving product from the methanol chromatography and rechromatographed on silica gel (100 g.) with mixtures of methanol and chloroform with 3% to 5% methanol. The product obtained from this column appeared as a broad streak on a silica gel thin layer chromatography plate eluted with 5% methanol-95% chloroform. It was crystallized from methanol-ethyl acetate to give in two crops: 0.388 g. of melting point 187.5°–188.5° C. and 0.123 g. of melting point 188°–189° C. of 8-chloro-1-[2-(dimethylamino)-1-methylethyl]-6-phenyl-4H-s-triazolo-[4,3-a][1,4]benzodiazepine. The analytical sample had a melting point of 187.5°–188.5° C.

Anal. Calcd. for $C_{21}H_{22}ClN_5$: C, 66.40; H, 5.84; Cl, 9.33; N, 18.43 Found: C, 66.20; H, 5.74; Cl, 9.42; N, 18.65

EXAMPLE 12

8-Chloro-1-[2-(diethylamino)ethyl]-6-phenyl-4H-s-triazolo[4,3-a][1,4]benzodiazepine In the manner given in Example 1, a solution of 8-chloro-1-methyl-6-phenyl-4H-s-triazolo[4,3-a][1,4]benzodiazepine in dimethylformamide, N,N,N',N'-tetraethyldiaminomethane and acetyl chloride (in 0.25 molar excess compared to the N,N,N',N'-tetraethyldiaminomethane) are reacted together to give 8-chloro-1-[2-(diethylamino)ethyl]-6-phenyl-4H-s-triazolo[4,3-a][1,4]benzodiazepine.

EXAMPLE 13

8-Bromo-1-[2-(dimethylamino)ethyl]-6-(2-pyridyl)-4H-s-triazolo[4,3-a][1,4]benzodiazepine In the manner given in Example 1, a solution of 8-bromo-1-methyl-6-(2-pyridyl)-4H-s-triazolo[4,3-a][1,4]benzodiazepine in dimethylformamide, N,N,N',N'-tetramethyldiaminomethane and acetyl chloride (in 0.1 molar excess compared to the N,N,N',N'-tetramethyldiaminomethane), are reacted together to give 8-bromo-1-[2-(dimethylamino)ethyl]-6-(2-pyridyl)-4H-s-triazolo[4,3-a][1,4]benzodiazepine.

EXAMPLE 14

8-Chloro-1-[2-(diethylamino)ethyl]-6-(2-pyridyl)-4H-s-triazolo[4,3-a][1,4]benzodiazepine In the manner given in Example 1, a solution of 8-chloro-1-methyl-6-(pyridyl)-4H-s-triazolo[4,3-a][1,4]benzodiazepine in dimethylformamide, N,N,N',N'-tetraethyldiaminomethane and acetylchloride (in 0.5 molar excess compared to the N,N,N',N'-tetraethyldiaminomethane) are reacted together to give 8-chloro-1-[2-(diethylamino)ethyl]-6-(2-pyridyl)-4H-s-triazolo[4,3-a][1,4]benzodiazepine.

EXAMPLE 15

8-Chloro-1-[2-(dimethylamino)ethyl]-6-(o-chlorophenyl)-4H-s-triazolo[4,3-a][1,4]benzodiazepine In the manner given in Example 1, a solution of 8-chloro-1-methyl-6-(o-chlorophenyl)-4H-s-triazolo[4,3-a][1,4]benzodiazepine in dimethylformamide, N,N,N',N'-tetramethyldiaminomethane and acetyl chloride (in 0.2 molar excess compared to the N,N,N',N'-tetramethyldiaminomethane) are reacted together to give 8-chloro-1-[2(dimethylamino)ethyl]-6-(o-chlorophenyl)-4H-s-triazolo[4,3][1,4]benzodiazepine.

EXAMPLE 16

8-Fluoro-1-[2-(dipropylamino)ethyl]-6-(o-fluorophenyl)-4H-s-triazolo[4,3-a][1,4]benzodiazepine In the manner given in Example 1, a solution of 8-fluoro-1-methyl-6-(o-fluorophenyl)-4H-s-triazolo[4,3-a][1,4]benzodiazepine in dimethylformamide, N,N,N',N'-tetrapropyldiaminomethane and acetyl chloride (in 0.5 molar excess compared to the N,N,N',N'-tetrapropyldiaminomethane) are reacted together to give 8-fluoro-1[2-(dipropylamino)ethyl]-6-(o-fluorophenyl)-4H-s-triazolo[4,3-a][1,4-benzodiazepine

EXAMPLE 17

8-Chloro-1-[2-(dimethylamino)ethyl]-6-(2,6-difluorophenyl)-4H-s-triazolo[4,3-a][1,4]benzodiazepine In the manner given in Example 1, a solution of 8-chloro-1-methyl-6-(2,6-difluoroethyl)-4H-s-triazolo[4,3-a][1,4]benzodiazepine in dimethylformamide, N,N,N',N'-tetramethyldiaminomethane and acetyl chloride (in 0.1 molar excess compared to the N,N,N',N'-tetramethyldiaminoethane) are reacted together to give 8-chloro-1-[2-(dimethylamino)ethyl]-6-(2,6-difluorophenyl)-4H-s-triazolo[4,3-a][1,4]benzodiazepine.

EXAMPLE 18

8-Nitro-1-[2-(dipropylamino)ethyl]-6-(2-pyridyl)-4H-s-triazolo[4,3-a][1,4]benzodiazepine In the manner given in Example 1, a solution of 8-nitro-1-methyl-6-(2-pyridyl)-4H-s-triazolo[4,3-a][1,4]benzodiazepine in dimethylformamide, N,N,N',N'-tetrapropyldiaminomethane and acetyl chloride (in 0.1 molar excess compared to the N,N,N'N'-tetrapropyldiaminomethane) are reacted together to give 8-nitro-1-[2-(dipropylamino)ethyl]-6-(2-pyridyl)-4H-s-triazolo[4,3-a][1,4]benzodiazepine.

EXAMPLE 19

8-Bromo-1-[2-(diethylamino)ethyl]-6-(o-fluorophenyl)-4H-s-triazolo[4,3-a][1,4]benzodiazepine In the manner given in Example 1, a solution of 8-bromo-1-methyl-6-(o-fluorophenyl)-4H-s-triazolo[4,3-a][1,4]benzodiazepine in dimethylformamide, N,N,N',N'-tetraethyldiaminomethane and acetyl chloride (in 0.5 molar excess compared to the N,N,N',N'-tetraethyldiaminomethane) are reacted together to give 8-bromo-1-[2-(diethylamino)ethyl]-6-(o-fluorophenyl)-4H-s-triazolo[4,3-a][1,4]benzodiazepine.

EXAMPLE 20

7-Chloro-1-[2-(dimethylamino)ethyl]-6-(o-chlorophenyl)-4-H-s-triazolo[4,3-a][1,4]benzodiazepine In the manner given in Example 1, a solution of 7-chloro-1-methyl-6-(o-chlorophenyl)-4H-s-triazolo[4,3-a][1,4]benzodiazepine in dimethylformamide, N,N,N',N'-tetramethyldiaminomethane and acetyl chloride (in 0.25 molar excess compared to the N,N,N',N'-tetramethyldiaminomethane) are reacted together to give 7-chloro-1-[2-(dimethylamino)ethyl]-6-(o-chlorophenyl)-4H-s-triazolo[4,3-a][1,4]benzodiazepine.

EXAMPLE 21

8-Methylthio-1-[2-(dimethylamino)ethyl]-6-phenyl-4H-s-triazolo[4,3-a][1,4]benzodiazepine In the manner given in Example 1, a solution of 8-methylthio-1-methyl-6-phenyl-4H-s-triazolo[4,3-a][1,4]benzodiazepine in dimethylformamide N,N,N',N',-tetramethyldiaminomethane and acetyl chloride (in 0.1 molar excess compared to the N,N,N',N',-tetramethyldiaminomethane) are reacted together to give 8-methylthio-1-[2-(dimethylamino)ethyl]-6-phenyl-4H-s-triazolo[4,3-a][1,4]benzodiazepine

EXAMPLE 22

8-Trifluoromethyl-1-[2-(dimethylamino)ethyl]-6-phenyl-4H-s-triazolo[4,3-a][1,4]benzodiazepine In the manner given in Example 1, a solution of 8-trifluoromethyl-1-methyl-6-phenyl-4H-s-triazolo[4,3-a][1,4]benzodiazepine in dimethylformamide, N,N,N',N'-tetramethyldiaminomethane and acetyl chloride (in 0.1 molar excess compared to the N,N,N', N'-tetramethyldiaminomethane) are reacted together to give 8-trifluoromethyl-1-[2-(dimethylamino)ethyl]-6-phenyl-4H-s-triazolo[4,3-a][1,4]benzodiazepine.

EXAMPLE 23

8-Trifluoromethyl-1-[2-(dipropylamino)ethyl]-6-(2-pyridyl)-4H-s-triazolo[4,3-a][1,4]benzodiazepine In the manner given in Example 1, a solution of 8-trifluoromethyl-1-methyl-6-(2-pyridyl)-4H-s-triazolo[4,3-a][1,4]benzodiazepine in dimethylformamide, N,N,N',N'-tetrapropyldiaminomethane and acetyl chloride (in 0.1 molar excess compared to the N,N,N',N'-tetrapropyldiaminomethane) are reacted together to give 8-trifluoromethyl-1-[2-(dipropylamino)ethyl]-6-(2-pyridyl)-4H-s-triazolo[4,3-a][1,4-]benzodiazepine.

EXAMPLE 24

9-Trifluoromethyl-1-[2-(diethylamino)ethyl]-6-phenyl-4H-s-triazolo[4,3-a][1,4]benzodiazepine In the manner given in Example 1, a solution of 9-trifluoromethyl-1-methyl-6-phenyl-4H-s-triazolo[4,3-a][1,4]benzodiazepine in dimethylformamide, N,N,N′,N′,-tetraethyldiaminomethane and acetyl bromide (in 0.2 molar excess compared to the N,N,N′,N′-tetraethyldiaminomethane) are reacted together to give 9-trifluoromethyl-1-[2-(diethylamino)ethyl]-6-phenyl-4H-s-triazolo[4,3-a][1,4]benzodiazepine.

EXAMPLE 25

8-Methylthio-1-[2-(dipropylamino)ethyl]-6-(2-pyridyl)-4-H-s-triazolo[4,3-a][1,4]benzodiazepine In the manner given in Example 1, a solution of 8-methylthio-1-methyl-6-(2-pyridyl)-4H-s-triazolo[4,3-a][1,4]benzodiazepine in dimethylformamide, N,N,N′,N′-tetrapropyldiaminomethane and trifluoroacetic anhydride (in 0.2 molar excess compared to the N,N,N′,N′-tetrapropyldiaminomethane) are reacted together to give 8-methylthio-1-[2-(dipropylamino)ethyl]-6-(2-pyridyl)-4H-s-triazolo[4,3-a][1,4]benzodiazepine.

EXAMPLE 26

8-Methylthio-1-[2-(diethylamino)ethyl]-6-phenyl-4H-s-triazolo[4,3-a][1,4]benzodiazepine In the manner given in Example 1, a solution of 8-methylthio-1-methyl-6-phenyl-4H-s-triazolo[4,3-a][1,4]benzodiazepine in dimethylformamide, N,N,N′,N′-tetraethyldiaminomethane and acetyl bromide (in 0.5 molar excess compared to the N,N,N′,N′-tetraethyldiaminomethane) are reacted together to give 8-methylthio-1-[2-(diethylamino)ethyl]-6-phenyl-4H-s-triazolo[4,3-a][1,4]benzodiazepine.

I claim:

1. An improved process for the production of compounds of the formula II:

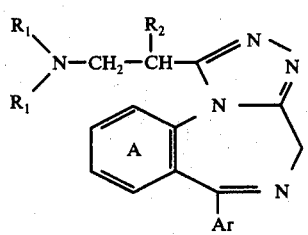

wherein $R_1$ is alkyl of 1 to 3 carbon atoms, inclusive; wherein $R_2$ is hydrogen, methyl or phenyl; wherein the ring A is unsubstituted, or monosubstituted with fluoro, chloro, bromo, nitro, trifluoromethyl, or methylthio; and wherein Ar is phenyl; o-chlorophenyl; o-fluorophenyl; 2,6-difluorophenyl or 2-pyridyl, which comprises reacting a compound of the formula I:

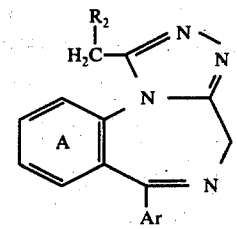

wherein ring A, Ar and $R_2$ are defined as above, with a dialkylmethyleneammonium salt wherein alkyl is of 1 to 3 carbon atoms, inclusive, in the presence of 0.05 to 0.5 moles of an acylating agent per 1 mole of the dialkylmethyleneammonium salt in which the acylating agent is selected from the group consisting of

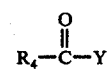

wherein $R_4$ is phenyl, or alkyl of 1 to 5 carbon atoms, inclusive, in which the alkyl moiety can be chlorinated or fluorinated and Y is chloro or bromo, or with an acid anhydride of the formula:

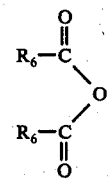

wherein $R_6$ is defined as a chloro or fluoro-substituted alkyl of 1 to 5 carbon atoms, or an alkyl chloroformate of the formula:

ClCOOR′ wherein R′ is a lower alkyl of 1 to 4 carbon atoms, to obtain the compound of formula II above.

2. The process of claim 1 wherein the dialkylmethyleneammonium salt is produced by treating a N,N,N′,N′-tetraalkyldiaminomethane with an acylating agent selected from the group consisting of

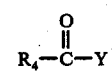

wherein $R_4$ is phenyl, or alkyl of 1 to 5 carbon atoms, inclusive, in which the alkyl moiety can be chlorinated or fluorinated and Y is chloro or bromo, or with an acid anhydride of the formula

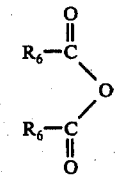

wherein $R_6$ is defined as a chloro or fluoro-substituted alkyl of 1 to 5 carbon atoms, or an alkyl chloroformate of the formula:

ClCOOR′ wherein R' is a lower alkyl of 1 to 4 carbon atoms, in 5%–50% stoichiometric excess and treating the mixture with a compound of formula I:

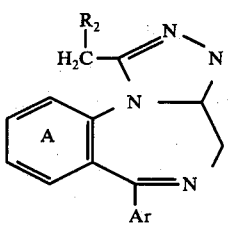

wherein $R_2$ is hydrogen, methyl or phenyl; wherein the ring A is unsubstituted, or substituted with fluoro, chloro, bromo, nitro, trifluoromethyl, or methylthio; and wherein Ar is phenyl, o-chlorophenyl, o-fluorophenyl, 2,6-difluorophenyl or 2-pyridyl.

3. The process of claim 1 wherein the dialkylmethyleneammonium salt is produced by treating N,N,N',N'-tetraalkyldiaminomethane together with the starting compound of the formula:

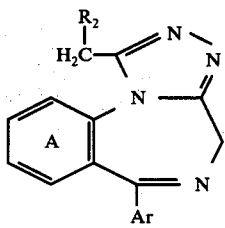   I wherein $R_2$ is hydrogen, methyl or phenyl; wherein the ring A is unsubstituted, or substituted with fluoro, chloro, bromo, nitro, trifluoromethyl or methylthio; and wherein Ar is phenyl, o-chlorophenyl, o-fluorophenyl, 2,6-difluorophenyl or 2-pyridyl, with an acylating agent selected from the group consisting of

wherein $R_4$ is phenyl, or alkyl of 1 to 5 carbon atoms, inclusive, in which the alkyl moiety can be chlorinated or fluorinated and Y is chloro or bromo, or with an acid anhydride of the formula:

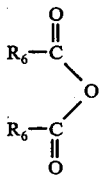

wherein $R_6$ is defined as a chloro or fluoro-substituted alkyl of 1 to 5 carbon atoms, or an alkyl chloroformate of the formula:

ClCOOR' wherein R' is a lower alkyl of 1 to 4 carbon atoms, in a 5%–50% stoichiometric excess.

4. A process for the preparation of 8-chloro-1-[2-(dimethylamino)ethyl]-6-phenyl-4H-s-triazolo[4,3-a][1,4]-benzodiazepine which comprises:
treating 8-chloro-1-methyl-6-phenyl-4H-s-triazolo[4,3-a][1,4]benzodiazepine with a dimethylmethyleneammonium salt in the presence of 0.05 to 0.5 mole of an acylating agent selected from the group consisting of

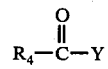

wherein $R_4$ is phenyl, or alkyl of 1 to 5 carbon atoms, inclusive, in which the alkyl moiety can be chlorinated or fluorinated and Y is chloro or bromo, or with an acid anhydride of the formula

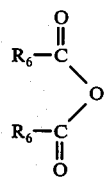

wherein $R_6$ is defined as a chloro or fluoro-substituted alkyl of 1 to 5 carbon atoms, or an alkyl chloroformate of the formula:

ClCOOR' wherein R' is a lower alkyl of 1 to 4 carbon atoms, per mole of dimethylmethyleneammonium salt to obtain 8-chloro-1-[2-(dimethylamino)ethyl]-6-phenyl-4H-s-triazolo[4,3-a][1,4]benzodiazepine.

5. The process of claim 2 wherein the dimethylmethyleneammonium salt is prepared by mixing N,N,N',N'-tetramethyldiaminomethane with an acylating agent selected from the group consisting of

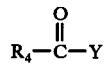

wherein $R_4$ is phenyl, or alkyl of 1 to 5 carbon atoms, inclusive, in which the alkyl moiety can be chlorinated or fluorinated and Y is chloro or bromo, or with an acid anhydride of the formula

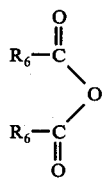

wherein $R_6$ is defined as a chloro or fluoro-substituted alkyl of 1 to 5 carbon atoms, or an alkyl chloroformate of the formula ClCOO R' wherein R' is a lower alkyl of 1 to 4 carbon atoms, and after the reaction has taken place to give the dimethylmethyleneammonium salt, adding 8-chloro-1-methyl-6-phenyl-4H-s-triazolo[4,3-a][1,4]benzodiazepine.

6. The process of claim 2 wherein the dimethylmethyleneammonium salt is made in situ from N,N,N',N'-tetramethyldiaminomethane and an acylating agent selected from the group consisting of

wherein $R_4$ is phenyl, or alkyl of 1 to 5 carbon atoms, inclusive, in which the alkyl moiety can be chlorinated or fluorinated and Y is chloro or bromo, or with an acid anhydride of the formula

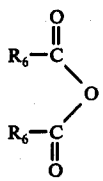

wherein $R_6$ is defined as a chloro or fluoro-substituted alkyl of 1 to 5 carbon atoms, or an alkyl chloroformate of the formula:

ClCOOR' wherein R' is a lower alkyl of 1 to 4 carbon atoms, in the present of 8-chloro-1-methyl-6-phenyl-4H-s-triazolo[4,3-a][1,4]benzodiazepine.

7. The process of claim 1 wherein the starting compound is of the formula:

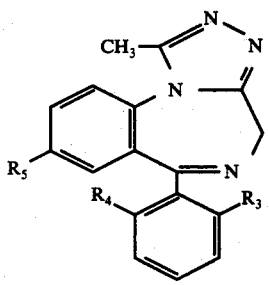

wherein $R_3$ is hydrogen, chloro or fluoro; wherein $R_4$ is hydrogen, or fluoro, providing $R_3$ is not chloro; and wherein $R_5$ is hydrogen, fluoro, chloro, trifluoromethyl or methylthio, the reactant is a dimethylmethyleneammonium salt and the final product is of formula IIA:

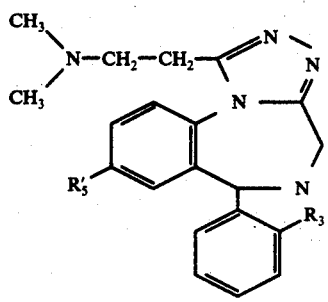

wherein $R_3$, $R_4$ and $R_5$ are defined as above.

8. The process of claim 1 wherein the starting compound is of the formula:

[structure shown]

wherein $R_3$ is hydrogen, chloro, or fluoro; and wherein $R_5'$ is chloro, fluoro, or trifluoromethyl, the reactant is a dimethylmethyleneammonium salt and the final product is of the formula IIB:

[structure IIB shown]

wherein $R_3$ and $R_5'$ are defined as above.

9. The process of claim 3 wherein the acylating agent is acetyl chloride.

10. The process of claim 9 wherein the reaction temperature is between $-10°$ C. and $+10°$ C.

11. The process of claim 5 wherein the acylating agent is acetyl chloride.

12. The process of claim 11 wherein the reaction temperature is between $-10°$ C. and $+10°$ C.

13. The process of claim 6 wherein the acylating agent is acetyl chloride.

14. The process of claim 13 wherein the reaction temperature is between $-10°$ C. and $+10°$ C.

* * * * *

UNITED STATES PATENT AND TRADEMARK OFFICE
CERTIFICATE OF CORRECTION

PATENT NO. : 4,075,221

DATED : 21 February 1978

INVENTOR(S) : Jackson B. Hester, Jr.

It is certified that error appears in the above—identified patent and that said Letters Patent is hereby corrected as shown below:

Column 11, line 49, "[1,4-benzodiazepine" should read -- [1,4]benzodiazepine --
Column 12, line 23, "-4-H-s-" should read -- -4H-s- --.

Signed and Sealed this

Third Day of November 1981

|SEAL|

Attest:

GERALD J. MOSSINGHOFF

Attesting Officer

Commissioner of Patents and Trademarks